United States Patent [19]

Campbell et al.

[11] Patent Number: 4,812,474
[45] Date of Patent: Mar. 14, 1989

[54] KOJIC ACID ETHER-ESTER DERIVATIVES

[75] Inventors: Arthur L. Campbell, Glenview; Masateru Miyano, Northbrook, both of Ill.

[73] Assignee: G. D. Searle & Co., Chicago, Ill.

[21] Appl. No.: 142,982

[22] Filed: Jan. 12, 1988

Related U.S. Application Data

[62] Division of Ser. No. 862,086, May 12, 1986, Pat. No. 4,735,964, which is a division of Ser. No. 641,229, Aug. 16, 1984, Pat. No. 4,603,144.

[51] Int. Cl.$^4$ .................... A61K 31/35; C07D 309/32
[52] U.S. Cl. ...................................... 514/460; 549/417
[58] Field of Search ........................ 514/460; 549/417

[56] References Cited

U.S. PATENT DOCUMENTS 3,152,148 10/1964 Easterly et al. .................... 549/417

Primary Examiner—Nicky Chan
Attorney, Agent, or Firm—Mary Jo Kanady; Paul D. Matukaitis

[57] ABSTRACT

Kojic acid ether-ester derivatives of formula I

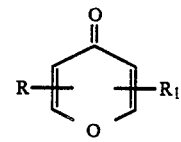

are useful pharmacological agents for the prevention, management or alleviation of elastase mediated diseases or conditions.

4 Claims, No Drawings

KOJIC ACID ETHER-ESTER DERIVATIVES

This is a division of application Ser. No. 06/862,086, filed May 12, 1986, now U.S. Pat. No. 4,735,964, which is a division of application Ser. No. 641,229 filed Aug. 16, 1984, now U.S. Pat. No. 4,603,144

BACKGROUND OF THE INVENTION

(1) Field of the Invention

The present invention relates generally to novel ether-esters derived from kojic acid. More particularly, the compounds of the invention are represented by the formula I

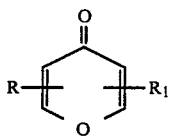

wherein R and $R_1$ are different and represent $—(CH_2)_n$-alkoxy of from about 10 to 20 carbon atoms; —COOH;

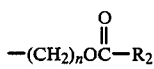

wherein $R_2$ is straight or branched chain alkyl of from about 1 to 6 carbon atoms; aralkyl of from about 6 to 15 carbon atoms; benzyloxy; or the group

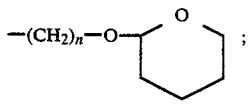

and n is 0 or 1; and the pharmaceutically acceptable non-toxic salts thereof.

The present invention is further directed to pharmaceutical compositions and methods for inhibiting or controlling physiological levels of active proteases, especially elastase, in biological tissues and, thus, the ultimate mitigation or prevention of elastase mediated connective tissue diseases or conditions. The pharmaceutical compositions comprise a pharmaceutically acceptable non-toxic carrier in combination with an active derivative of formula I. The method comprises the administration of a therapeutically, e.g., anti-inflammatory, effective amount of a derivative of formula I.

Proteases or protein splitting enzymes are proteins whose function is to alter or decompose other proteins by splitting them into fragments. They are essential in a variety of physiological activities such as digestion, formation and dissolution of blood clots, the repair or removal of damaged or injured tissues, the removal of tissue debris, the immune reaction to foreign cells and organisms and inflammatory processes, among others.

While the proteases serve important biological functions, they are controlled by a mechanism which prevents them from indiscriminately destroying any protein within their presence. The mechanism includes protease inhibitors which bind with the proteases and prevent their protein fragmentation action. For further information, see "A Family of Protein cutting Proteases", Scientific American, R. M. Stroud, July 1974, pages 74–78.

In general, proper function of the control mechanism is important for the health of the host organism. A protease-inhibitor imbalance can produce an excess of protease and permit the undesirable degradation of structural proteins such as elastin, collagen, and proteoglycan. It can be seen that dysfunction of the control mechanism can lead to connective tissue destruction and disease.

The protease, elastase, is believed to play an important part in the etiology of inflammatory connective tissue disease. It fragments elastin, a functional protein component of connective tissue, as well as other proteins and, hence, can reduce the elastic expansion and contraction of the lungs and the cardiovascular system and can destroy the resiliency and elasticity of joints. As a result, the function, elasticity and resiliency of organs containing elastin can be adversely affected and the organs will eventually undergo trophic changes, including the loss of elastic tissue, as occurs in such diseases as rheumatoid arthritis, pulmonary emphysema, chronic obstructive pulmonary disease, atherosclerosis, pseudoxanthoma elasticum, X-linked cutis laxa, Menke's kinky-hair syndrome, and Ehlers-Danlos syndrome, Type V.

Further indications of the relation between elastase and connective tissue disease have been shown by animal model studies and by joint tissue studies. For example, papain and porcine pancreatic elastase are elastase-like proteases which have been used experimentally to produce emphysema-like disease in animal models. Human leukocyte elastase, extracted from human polymorphonuclear leukocytes, has also been instilled intratracheally into animals to produce a disease resembling human emphysema. The physiological and morphological results of elastase induced emphysema in such animal models and the corresponding animal symptoms and biochemistry have been compared to the disease in man, and these tests have shown an association between elastase and emphysema; see Sandberg, et al., The New England Journal of Medicine, 304, 566, (1981).

Rheumatoid arthritis is another example of a disease which has been linked to inhibitor-protease imbalance. In the course of this disease, polymorphonuclear leukocytes are released and enter acute inflammatory exudates to phagocytize immune reactants and cellular material thereby releasing elastase. When the elastase release overwhelms the inhibitors present in the local tissue, phagocytosis proceeds not only upon material which should be removed but upon the healthy tissue and hence causes greatly enhanced tissue damage. The major portion of this proteolytic activity has been attributed to elastase. See, for example, Janoff, Biochem. J., 114, 157 (1969) and Wong, Travis, Biochem. Biophys. Res. Comm., 96, 1449 (1980).

Research into inflammatory diseases involving proteolytic enzymes has sought to isolate and characterize endogenous protease inhibitors present in biological tissues. Human serum $\alpha_1$-antitrypsin and $\alpha_2$-macroglobin are two known endogenous inhibitors. Synthetic inhibitors have also been studied; see U.S. Pat. No. 4,195,023. In general, however, little work has been done to produce a synthetic inhibitor which is highly active, produces desirable results in models of elastase related disease and is relatively free of harmful side effects.

State of the Art

U.S. Pat. No. 3,968,236 discloses 2-aminomethyl-5-hydroxy-4H-pyran-4-one and derivatives having skeletal muscle relaxant properties. No ether-ester(s) (or ester precursors) are disclosed and the compounds are not indicated to have any anti-inflammatory/elastase inhibitory properties.

2-Iodomethyl-5-hydroxy-6-bromo-4-pyrone, 2-iodomethyl-5-hydroxy-4-pyrone and related 2-, 5-, 6-substituted kojic acid derivatives which are not ether-ester derivatives of formula I are disclosed in *Chem. Abstracts*, Vol. 78, 119672w as having antibacterial activity.

U.S. Pat. No. 4,278,656 discloses aliphatic mono- and di-esters, particularly diesters, of kojic acid as useful in skin whitener cosmetic compositions. None of the compounds disclosed comprise derivatives wherein one of the substituents is an ether.

5-Acetoxy-2-(methoxymethyl)-4H-pyran-4-one is disclosed as one of three reaction products formed by the acetylation of 1,3-di-O-acetyl-4,6,di-O-methyl-α-D-arabino-hexopyranosulose in *Chem. Abstracts*. Vol. 78, 124816a. No long-chain aliphatic ether-esters or elastase inhibitory properties thereof are disclosed.

SUMMARY OF INVENTION

It is, therefore, an object of the invention to provide a synthetic inhibitor of proteolytic enzymes which will be effective for the alleviation or prevention of diseases associated with protease-inhibitor control imbalance. A further object is the production of a synthetic inhibitor compound which inhibits elastase action. Yet another object of the invention is the production of a synthetic inhibitor of elastase which has specific activity and exhibits few side effects.

These and other objects are achieved according to the compounds, compositions and methods of the invention comprised of the kojic acid ether-ester derivatives of formula I having elastase inhibitor/anti-inflammatory activity

DETAILED DESCRIPTION OF THE INVENTION

Proteolytic enzymes are of great importance for all mammalian organisms. The many physiological and biochemical. processes in which they function require substantial control of their proteolytic activity. While the proteolytic enzyme hydrolyze peptide bonds of proteins, the nature of the active catalysis site of each type of proteolytic enzyme varies so that the electrostatic, hydrophilic and lipophilic forces which bind an enzyme to its substrate can be utilized to permit specific rather than general protein hydrolysis. Further control is produced by protease inhibitors which have evolved configurations within the binding regions which closely resemble those of bound substrate proteins. Since proteolytic enzymes are ubiquitous and serve such an important function for biological organisms, a non-specific synthetic inhibitor which prohibits the action of many proteolytic enzymes would serve little purpose as a drug. Instead, inhibition or control of a specific proteolytic enzyme is the desired goal.

It has now been found, in accordance with the present invention, that the compounds of formula I advantageously selectively inhibit the proteolytic enzyme elastase from human leukocytes. Without wishing to be limited to any particular mechanism of action, it is presently believed that the probable mechanism of action of the compounds of the present invention is through species specific substrate elastase binding. the kojic acid ether ester derivatives of the invention are comprised of lipophilic groups, and the sterically large lipophilic ether group in particular is considered important for elastase substrate binding. Moreover, the ether-esters of the present invention have been found to be very stable to liber esterase degradation which constitutes one of the advantageous aspects of the invention in providing relatively long-acting anti-inflammatory activity.

The compounds of the present invention are comprised of those having the formula I.

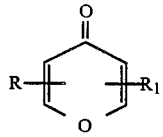

wherein R and $R_1$ are different and represent —($CH_2$)$_n$— alkoxy of from about 10 to 20 carbon atoms; —COOH; —($CH_2$)$_n$—

wherein $R_2$ is straight or branched chain alkyl of from about 1 to 6 carbon atoms; aralkyl of from about 6 to 15 carbon atoms; benzyloxy; or the group

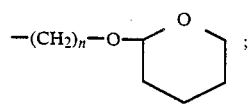

and n is 0 or 1; and the pharmaceutically acceptable non-toxic salts thereof.

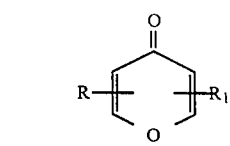

wherein R and $R_1$ are different and represent —($CH_2$)$_n$— alkoxy of from about 10 to 20 carbon atoms; —COOH; —($CH_2$)$_n$—

wherein $R_2$ is straight or branched chain alkyl of from about 1 to 6 carbon atoms; aralkyl of from about 6 to 15 carbon atoms; benzyloxy; or the group

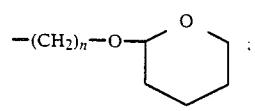

and n is 0 or 1; and the pharmaceutically acceptable non-toxic salts thereof.

Of the foregoing compounds, particularly preferred for use in the elastase inhibitory/anti-inflammatory pharmaceutical compositions and methods of the invention are those compounds of formulas II and III and the pharmaceutically acceptable nontoxic salts or adducts thereof:

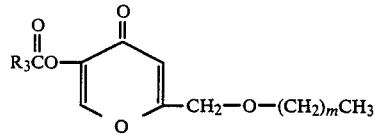
(II)

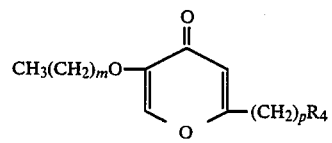
(III)

wherein
$R_3$ represents straight or branched chain alkyl of from 1 to 6 carbon atoms;
$R_4$ represents

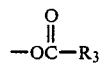

wherein $R_3$ is as defined before; or —COOH when p is O; and
m is 13 to 17 and p is 0 or 1.

Exemplary of particularly preferred substituents within the foregoing structural definitions for formulas I and II are as follows:
$R_3 =$ —CH(CH$_3$)$_2$, —C(CH$_3$)$_3$, —CH$_2$CH(CH$_3$)$_2$,

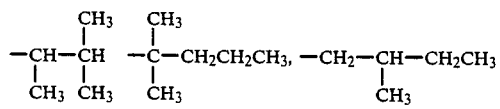

$R_4 =$

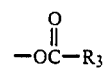

when p=1, or —COOH when p=0.

As used herein, the expression "alkoxy" in reference to the defined groups includes straight or branched chain carbon-carbon linkages. Preferred alkyl moieties thereof include dodecyl, tridecyl, tetradecyl, pentadecyl, hexadecyl and heptadecyl and the corresponding branched alkanes.

Preferred groups corresponding to the $R_2$ or $R_3$ moieties of the

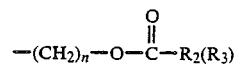

substituents in formulas I, II or III include isopropyl, isobutyl, sec-butyl, tert-butyl, isopentyl, 1-methylbutyl, neopentyl, 1,1-dimethyl-butyl and 1-methyl-2,2-dimethyl ethyl.

The compounds of the invention can be facilely prepared by synthetic methods known in the art, or modifications thereof, from available starting materials. The following general reaction schemes A and B depict the starting materials, reagents and general reaction conditions for preparing the compounds of the invention. The overall process of scheme A comprises a modified Williamson ether synthesis wherein benzyl kojic acid is reacted with a preselected long chain alkyl iodide followed by debenzylation/acylation. In scheme B, it is noted that the reaction may proceed to either the acylated ether derivatives (i.e., ester) or via Jones oxidation to the carboxylic acid ether derivatives.

SCHEME A

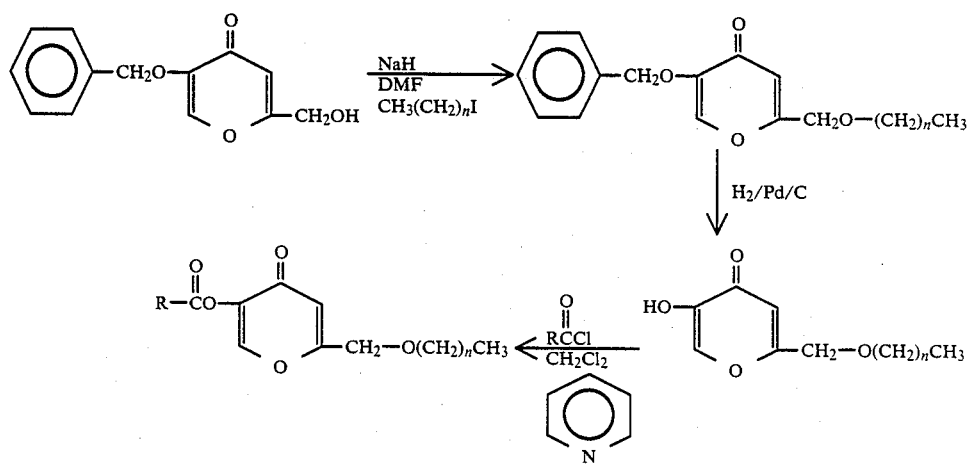

SCHEME B

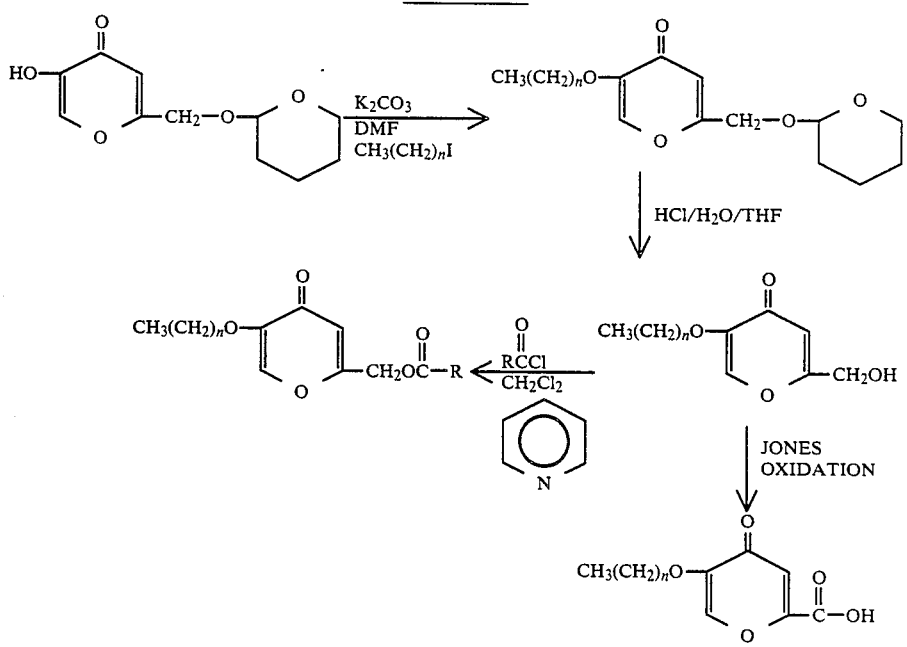

Isolation and purification procedures for the reaction products of schemes A and B will follow conventional practices. For instance, water-organic solvent phase extraction, recrystallization and chromatography on columns such as silica gel or cross-linked dextran gel can be utilized to isolate and purify the derivatives of the invention.

Further, it will be appreciated by those skilled in the art that the compounds of the present invention may be prepared in various salt forms and, as used herein, the expression "pharmaceutically acceptable non-toxic salts" is intended to include all those salts or adducts capable of being formed with the present compounds and substituted derivatives thereof in accordance with the invention without materially altering the chemical structure or pharmacological activity of the parent compounds. For example, alkali metal salts of carboxylic acid derivatives of the invention may be obtained by reaction with suitable bases, e.g., sodium hydroxide, potassium hydroxide, etc. Likewise alkaline earth metal salts, acid addition salts and the like may be obtained, where necessary to, for instance, alter solubility properties, etc.

During the progression of connective tissue diseases such as emphysema, arthritis, atherosclerosis and others, vast numbers of human protease secreting cells, for example, immune system cells such as neutrophils, are believed to be attracted to the diseased tissue where they engage in phagocytosis of locally generated complexes and tissue debris. During this process proteolytic enzymes are released into the intercellular spaces to promote phagocytosis. These enzymes, such as elastase, have the capacity to degrade connective tissue, bronchial collagenous membranes, synovial cartilage, and arterial elastic lamellae. Although this action is normal, protease imbalance and a subsequent overproduction of active protease is believed to contribute in a major way to irreversible destruction of the tissue especially in chronic inflammatory conditions. Consequently, controlling the protease imbalance with an inhibitor which mimics natural, physiological control is helpful for the prevention or alleviation of protease related diseases.

The derivatives of the invention are such protease inhibitors and act as pharmacologically active agents for the prevention or alleviation of protease related diseases. These derivatives can prevent tissue injury by their action as controlling inhibitors of active proteolytic enzymes. In particular, the derivatives are useful to prevent or alleviate malconditions related to or arising from human leukocyte elastase imbalance and harmful degradation of elastin and other proteins. Such diseases would include emphysema, atherosclerosis, connective tissue disease, rheumatoid arthritis, rheumatoid joint disease, pseudoxanthoma elasticum, X-linked cutis laxa, Menke's kinky-hair syndrome and Ehlers-Danlos syndrome, Type V as well as other diseases resulting from the harmful effect of elastase.

Several biochemical and animal model tests can be used to examine the ability of the derivatives of the invention to prevent or alleviate the harmful biological action of elastase. The biochemical assays permit direct measurement of drug controlled inhibition of elastase fragmentation of proteins. Typical tests include a chymotrypsin/t-Boc-Tyr-p-Nitrophenyl ester incubation, a human leukocyte elastase-Methoxysuccinyl-Ala-Ala-Pro-Val-Nitroanilide incubation and a hog pancreatic elastase/t-Boc-L-Ala-p-Nitrophenol ester incubation. In these tests, protease reaction with the substrate is measured in the presence and absence of the drug to be tested. Inhibition of protease action is indicated by a decrease in the amount of substrate fragmented. The basic parameters for such biochemical assays have been reported in the literature: *J. Biol. Chem.*, 255, 5435 (1980); *Biochem. Biophys Acta.*, 268, 257 (1973); Anal. *Biochem.* 48,9 (1972); and *Biochemistry*, 20, 3675 (1981).

In general, in vivo animal model tests will also permit estimation of drug controlled inhibition of protease action and in addition allow assessment of the decrease in tissue damage caused as a result of drug-protease interaction. Some animal tests commonly used include emphysema models such as mouse lung challenge with aspirated elastase solution and mouse or hamster intrabronchial challenge with papain, porcine pancreatic elastase or neutrophil elastase. In these procedures, the test drug is administered shortly before or after protease challenge, the animal is examined for respiratory compliance and sacrificed about 6-10 days later, and the lungs examined for lesions. Since it is believed that the compounds of formula I promote specific inhibition of neutrophil elastase, animal model tests would employ this elastase in order to develop an estimate of derivative activity. Such methods have been described in Am. Rev. Resp. Dis., 121, 1025 (1980); Lab. Invest., 34, 372 (1976); New Eng. J. Med., 304, 566 (1981); U.S. Pat. No. 4,193,023.

Examination of the derivatives of the invention in a selection of these tests has shown that they are therapeutically active compounds useful for the treatment of elastase mediated disease conditions. In particular, the derivatives of the invention are active inhibitors of human leukocyte elastase in the biochemical human leukocyte elastase-substrate assay while showing much lower inhibition in the chymotrypsin and hog pancreatic elastase biochemical assays. The derivatives also show few side effects as they do not produce significant activity in such tests as mouse diuresis and hCG stimulation of luteal cell progesterone production as well as other similar biological test screens.

The derivatives of the invention can be used in the treatment of emphysema, arthritis, atherosclerosis and other connective tissue diseases. Although the treatment of an individual patient suffering such a malady will be based upon his unique condition and upon the judgment of his attending physician, in general, the derivatives can be administered in doses and by routes which would be effective for the alleviation or prevention of such diseases. For treatment of arthritis, atherosclerosis and other internal connective tissue organ diseases, therapeutically effective amounts of the derivatives which would substantially inhibit elastase action may be injected intravenously, subcutaneously or intramuscularly. For treatment of acute, localized arthritis, therapeutically effective amounts of the derivatives which would substantially inhibit elastase action may be injected directly into the inflamed tissue, e.g., intra-articular, or may be administered by any of the aforementioned routes. For treatment of emphysema, therapeutically effective amounts of the derivatives which would substantially inhibit elastase action may be administered as a bronchial aspiration or mist directly to the lung or may be administered topically by slow release from rate controlled release transdermal delivery systems. For treatment of chronic dermal connective tissue malconditions, therapeutically effective amounts of the derivatives which would substantially inhibit elastase action may be applied topically or systemically by injection routes.

With these general guidelines in mind, the compounds for use in the elastase inhibitory pharmaceutical compositions and methods of the present invention are administered to an animal in need thereof in an amount sufficient to promote therapeutically effective elastase inhibition. The following dosage ranges may be employed as therapeutically effective elastase inhibitors in the treatment, management or alleviation of such elastase mediated conditions, diseases or disorders. Injection may be accomplished with a dose of about 50 to 500 mg per dosage unit with about 3 to 4 doses per day being given. Bronchial administration may be accomplished with aerosols or mists containing from about 0.1 to 10 percent derivative with a dose of about 5 to 200 mg per dosage unit being given from 2 to 6 times per day. Topical or transdermal administration may be accomplished with a dose of about 5 to 500 mg per dosage unit with about 1 to 3 applications per day. Variation and adjustment in dosing and administration will follow parameters known for each route of administration.

According to the invention the derivatives may be used either alone or in combination with a suitable pharmaceutical carrier. Used alone they may be administered as an alcoholic or aqueous solution, suspension or dilution at the appropriate dosage level and concentration. The character of such solutions will be adjusted for the route of administration desired.

The derivatives may be combined with such pharmaceutical carriers as: elixirs, suspending agents, diluents, starches, sugars, absorbing agents, wetting agents, isotonic agents, drying agents, waxing agents, solubilizing agents, dissolving aids, disintegrating aids, transport agents, and other similar pharmaceutical agents known to those skilled in the art. Examples include agar, pectin, acacia, ethanolic solutions, citric-carbonate buffers, isotonic solutions, peanut oil, olive oil, sesame oil, methyl cellulose, polyvinylpyrrolidine, cocoa butter, polyethylene glycol, and other similar types of well known pharmaceutical carriers, adjuvants, excipients, etc. (collectively referred to herein as "carriers").

Solutions, suspensions or dilutions of the compounds of the invention and pharmaceutical compositions of the invention may be formulated using appropriate known pharmaceutical methods to produce dosage forms appropriate for the desired route of administration. Such forms include sterile or isotonic solutions, injectable solutions, aerosol emulsions, liquid suspensions, troches, suppositories, sustained-release micro-encapsulation using pharmacologically acceptable sustained release polymers, and other similar formulations and or otherwise dosed medicaments known to those skilled in the art. When used intrabronchially, the formulation may be sprayed with an inhaler, atomizer, nebulizer and the like.

The following non-limiting examples will further illustrate to those skilled in the art the details for the preparation and biological testing of the derivatives of the invention. All temperatures are in °Celsius unless otherwise stated.

EXAMPLE 1

5-Benzyloxy-2-Hydroxymethyl-4-Pyrone (Intermediate)

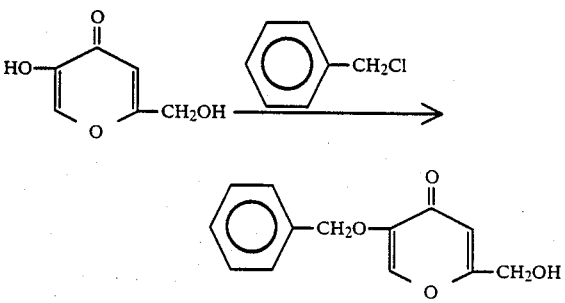

Kojic acid (17.05 g, 0.120 mole) was suspended in methanol (170 ml), H$_2$O (17 ml) and sodium hydroxide (5.14 g, 0.128 mole) added and the mixture allowed to stand. To the resulting solution, benzyl chloride (17.5 g, 0.138 mole) was added dropwise and the solution refluxed for 4.5 h. and cooled. The resulting brown solution was poured into 200 ml H+/H2O. The precipitate was filtered and stored at 65° C. overnight to give 22.38 g of the title compound as a yellow crystalline solid (m.p. 128°-130° C.).

Calculated for $C_{13}H_{12}O_4$: C, 67.23; H, 5.21. Found: C, 67.24; H, 5.05.

No IR;

NMR (DMSO-$d_6$) 80 MHz=4.27 (d, J=6), 4.93 (S, 2H), 6.30 (S), 7.35 (broad S, 5H), 8.12 (S) ppm.

From the foregoing reactant, the ether-ester derivatives of formulas I and II may be prepared according to synthesis scheme A set forth above.

EXAMPLE 2

5-Hydroxy-2-Tetrahydropyranyloxymethyl-4-pyrone (Intermediate)

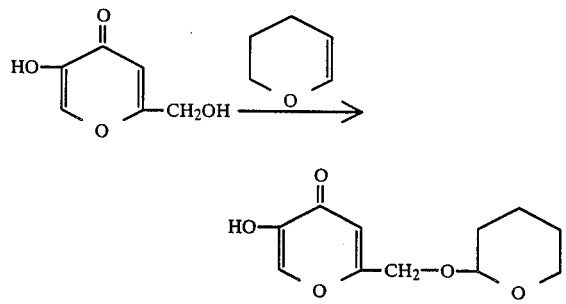

To a solution of 56.8 g of 5-hydroxy-2-hydroxymethyl-4-pyrone (kojic acid) in 2 L of methylene chloride, 0.4 g of p-toluenesulfonic acid monohydrate was added and the mixture was stirred for 1.5 h. The reaction mixture was extracted with 3% sodium hydroxide solution twice and then the combined aqueous phase was neutralized to pH 8 with 0.5M sodium dihydrogen phosphate. An extractive work-up (methylene chloride) follwed by recrystallization afforded 67 g (75%) of the title compound (mp 94° C.), NMR (CDCl3) 60 MHz: 4.32 (d, J=14, 1H, right hand of AB pattern), 4.61 (d, J=14, left half of AB pattern), 4.73 (broad S, 1H, acetal H), 6.60 (S, 1H, H-3), 7.86 (S, 1H, H-5) ppm; IR (CHCl3) 3430, 1640, 1600 cm$^{-1}$/UV (MeOH): 270 nm (Σ7,400).

Calculated for $C_{11}H_{14}O_5$: C, 58.40; H, 6.24. Found: C, 58.23; H, 6.35.

From the foregoing reactant, the ether-ester derivatives corresponding to formula III may be prepared according to synthesis scheme B set forth above.

EXAMPLE 3

General Procedure for Kojic Acid Hydroxymethyl Ether Formation with Long Chain Alkyl Iodides (Modified Williamson ether synthesis)

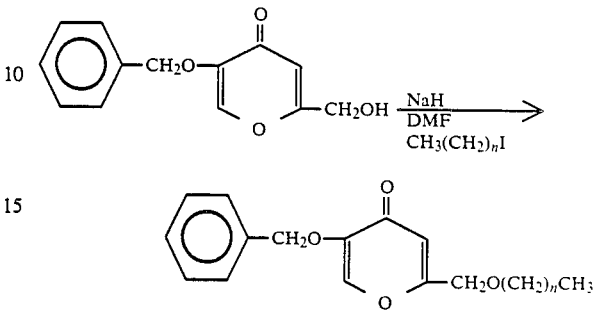

To NaH (0.3 g, 12.5 mmol.), washed with dry pentane (3×10 ml), was added DMF (20 ml) and the alkyl iodide (30 mmol) in THF (20 ml) followed by the slow addition of the benzyl kojic acid in DMF (15 ml) via a motor driven syringe (0.3 ml/min). The dark brown solution was stirred at 25° C. for 18 hr, then quenched with H2O (5.0 ml). The resultant solution was poured into EtAc (500 ml) and washed with water (3×200 ml), saturated NaCl (100 ml), dried (K2CO3) and concentrated to provide a brown oil. Titration of this oil with cold cyclohexane provided a solid which is recrystallizable from cyclohexane. Alternatively the crude oil can be purified by using a Waters Prep 500A Chromatograph (silica, EtAc/hexane: 3/7, 250 ml/min).

| For n = | 13 | yield 57% |
|---|---|---|
| | 15 | 70% |
| | 17 | 57% |

EXAMPLE 4

General Procedure for Debenzylation of Kojic Acid Ethers

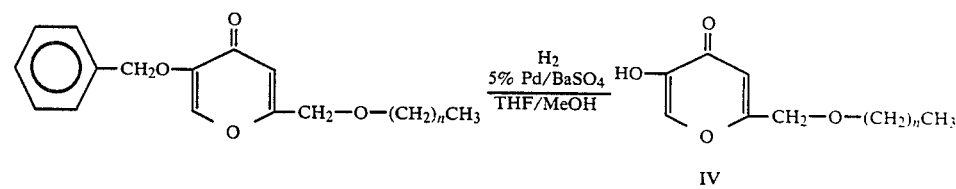

The benzyl kojic acid ether (10 mmol.) in THF/MeOH: 1/1 (236 ml) was hydrogenated (5% Pd/BaSO4, 0.9 g) at 25° C. and 2 psi until the theoretical amount of hydrogen had been absorbed (~1.0 hr). The catalyst was removed by filtration and the solvent removed in vacuo. The solid residue was recrystallized from cyclohexane to provide analytically pure material.

| yield for n = | 13 | 95% |
|---|---|---|
| | 15 | 94% |
| | 17 | 97% |

EXAMPLE 5

General Procedure for Acylating Kojic Acid Ethers

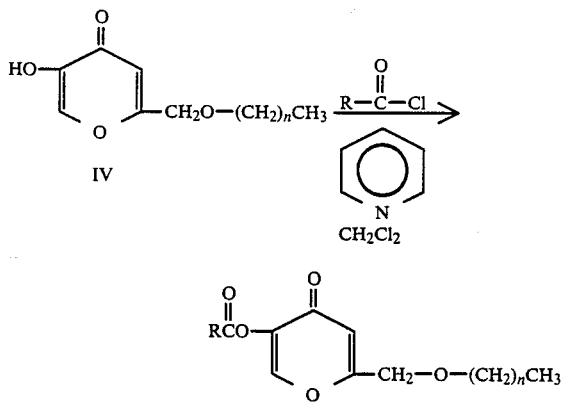

To the kojic acid ether IV (1.0 mmol) in CH$_2$Cl$_2$ (4.0 ml) cooled to 0° C. was added pyridine (5.0 mmol) followed by a solution of the acid chloride (1.5 mmol) in CH$_2$Cl$_2$ (2.0 ml). This mixture was allowed to slowly warm to 25° C. and stirring continued overnight. The reaction mixture was quenched with H$_2$O (2.0 ml), and after stirring for 10 min., the aqueous phase was extracted with CH$_2$Cl$_2$ (3×10 ml). The organic phases were combined, washed with 10% HCl (50 ml), H$_2$O (25 ml), saturated NaHCO$_3$ (25 ml), saturated NaCl (25 ml), dried (MgSO$_4$) and concentrated to provide crude solids. Purification was accomplished by radial chromatography (Chromatotron) on silica gel.

This same procedure was used for acylating kojic acid ethers in Scheme B as illustrated in the following examples.

EXAMPLE 6

General Procedure for Kojic Acid 5-Hydroxy Ether Formation with Long Chain Alkyl Halides

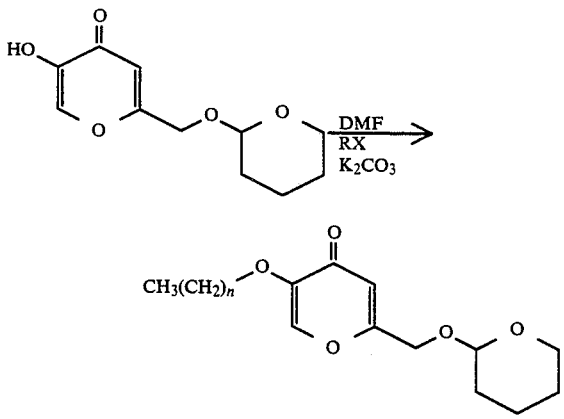

To a solution of 5-hydroxy-2-tetrahydro pyranyloxymethyl-4-pyrone (1.0 g, 4.4 mmol) and the alkyl halide (10.0 mmol) in DMF (20 ml) was added finely ground potassium carbonate (1.0 g, 7.2 mmol). This heterogenous mixture was stirred at 25° until reaction was complete (4–6 hrs) as determined by TLC (ETAC/hexane: 3/7). The solution was filtered, diluted with ether, (200 ml), washed with H$_2$O (3×100 ml), sat'd NaCl (1×100 ml), and dried (K$_2$CO$_3$). Concentration in vacuo, provided an oily solid which was purified using the Waters Prep 500A Chromatograph (ETAC/hexane: 3/7, 250 ml/min). Using cetyl iodide (n=15), Example 21, 1.45 g (73%) of a white solid was obtained.

EXAMPLE 7

Preparation of 2-Hydroxymethyl-5-Alkyloxy-4-Pyrone from 5-Alkyloxy-2-Tetrahydropyranyloxymethyl-4-Pyrone

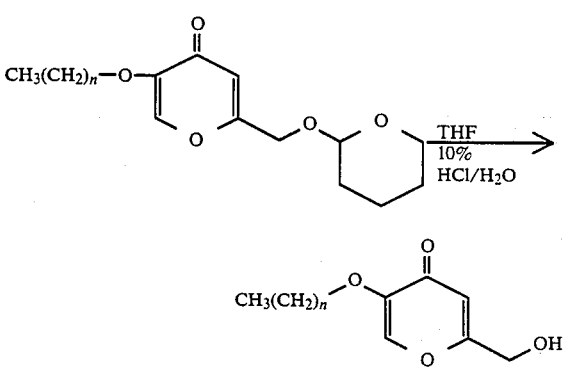

A solution of 5-hexadecyloxy-2-tetrahydro pyranyloxymethyl-4-pyrone (1.1 g, 2.5 mmol) and HCl (10% in H$_2$O, 10 ml) in THF (30 ml) was stirred at 25° overnight. TLC (ETAC/hexane: 3/7) indicated reaction was complete. The solution was diluted with ether (200 ml), washed with H$_2$O (3×50 ml), 10% NaHCO$_3$ (1×50 ml), sat'd NaCl (1×100 ml), dried (K$_2$CO$_3$) and concentrated to provide 0.88 g (98%) of 2-hydroxymethyl-5-hexadecyloxy-4-pyrone as a pure white solid mp 68.0°–69.5°.

EXAMPLE 8

Preparation of 2-Carboxy-5-Hexadecyloxy-4-Pyrone

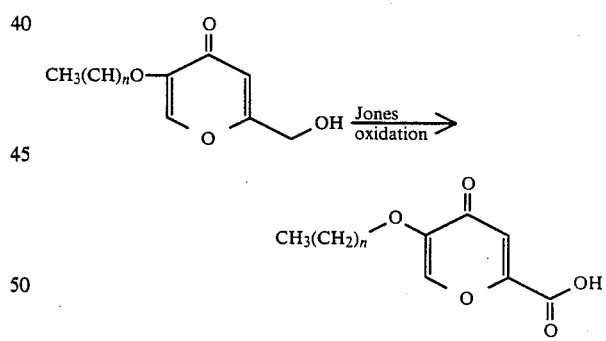

To a solution of 2-hexadecyl-5-hydroxy methyl-4-pyrone (117 mg, 0.3 mmol) in acetone (5 ml) was added Jones Reagent (2.67 mmol/ml, prepared according to Fieser & Fieser, Vol. I, p 142) dropwise until the orange color persisted. Stirring was continued at 25° for 30 min. and then isopropanol (1.0 ml) was added. After an additional 15 min. of stirring at 25° the green chromium salts were removed by filtration. The solvent was removed in vacuo and the greenish residue was titrated with EtAC and filtered. Removal of the ethyl acetate under a stream of nitrogen provided 100.0 mg (82%) of 2-carboxy-5-hexa decyloxy-4-pyrone as a white solid mp 126.5°–130.5°.

Utilizing the general synthesis methods of reaction schemes A and B and the starting reactants and conditions illustrated in Examples 1 through 8, the intermediates and derivatives set forth in Table I below were prepared.

TABLE 1

| EXAMPLE NO. | Structure | mp. (°C.) | IR | NMR (CDCl$_3$) |
|---|---|---|---|---|
| 9. | Ph-CH$_2$O-[pyran-4-one]-CH$_2$O(CH$_2$)$_{13}$CH$_3$<br>5-(phenylmethoxy)-2-[(tetradecyloxy)methyl]-4H—pyran-4-one<br>Analysis calc'd for C$_{27}$H$_{40}$O$_4$: C, 75.66; H, 9.41<br>Found: 75.46; H, 9.52 | 75-76 | (CHCl$_3$) 3010, 2940, 2865, 1658, 1629, 1198, 1163 cm$^{-1}$ | 0.88 (t, 3H), 1.26 (S, 24H), 1.4-1.7 (m, 2H), 3.47 (t, 3H), 4.22 (S, 2H) 5.05 (S, 2H), 6.44 (S, 1H), 7.33 (S, 5H), 7.49 (S, 1H) |
| 10. | Ph-CH$_2$O-[pyran-4-one]-CH$_2$O(CH$_2$)$_{15}$CH$_3$<br>2-[(hexadecyloxy)methyl]-5-(phenylmethoxy)-4H—pyran-4-one<br>Analysis Calc'd for C$_{29}$H$_{44}$O$_4$: C, 76.27; H, 9.21<br>Found: C, 76.11; H, 9.99 | 78.5-79.5 | (KBr Pellet) 3100, 2925, 2860, 1655, 1620, 1600, 1265, 1220 cm$^{-1}$ | 0.87 (t, 3H), 1.25 (S, 26H), 1.4-1.7 (M, 2H), 3.46 (t, 2H), 4.22 (S, 2H), 5.10 (S, 2H), 6.42 (S, 1H), 7.32 (S, 5H), 7.48 (S, 1H) |
| 11. | Ph-CH$_2$O-[pyran-4-one]-CH$_2$O(CH$_2$)$_{17}$CH$_3$<br>2-[(octadecyloxy)methyl]-5-(phenylmethoxy)-4H—pyran-4-one<br>Analysis calc'd for C$_{31}$H$_{48}$O$_4$: C, 76.82; H, 9.98<br>Found: C, 76.61; H, 10.07 | 82-83 | (CHCl$_3$) 3010, 2940, 2865, 1659, 1629, 1198, 1162 cm$^{-1}$ | 0.88 (t, 3H), 1.27 (S, 30H), 1.4-1.7 (m, 2H) 3.48 (t, 2H), 4.23 (S, 2H), 5.05 (S, 2H) 6.44 (S, 1H), 7.34 (S, 5H), 7.49 (S, 1H) |
| 12. | HO-[pyran-4-one]-CH$_2$O(CH$_2$)$_{13}$CH$_3$<br>5-hydroxy-2-[(tetradecyloxy)methyl]-4H—pyran-4-one<br>Analysis calc'd for C$_{20}$H$_{34}$O$_4$: C, 70.97; H, 10.12<br>Found: C, 70.60; H, 10.42 | 74-76 | (CHCl$_3$) 3418, 2930, 2855, 1655, 1630, 1460, 1255, 1150 cm$^{-1}$ | 0.88 (t, 3H), 1.25 (S, 22H), 1.4-1.75 (M, 2H), 3.50 (t, 2H), 4.25 (S, 2H), 6.51 (S, 1H), 7.81 (S, 1H) |
| 13. | HO-[pyran-4-one]-CH$_2$O(CH$_2$)$_{15}$CH$_3$<br>5-hydroxy-2-[(hexadecyloxy)methyl]-4H—pyran-4-one<br>Analysis calc'd for C$_{22}$H$_{38}$O$_4$: C, 72.09; H, 10.45<br>Found: C, 72.16; H, 10.46 | 80-81 | (KBr pellet) 3230, 2918, 2848, 1650, 1625, 1460, 1240, 1095, 894 cm$^{-1}$ | 0.85 (t, 3H); 1.28 (S, 26H), 1.60 (m, 2H), 3.50 (t, 2H), 4.30 (S, 2H), 6.50 (S, 1H), 7.80 (S, 1H) |
| 14. | HO-[pyran-4-one]-CH$_2$O(CH$_2$)$_{17}$CH$_3$<br>5-hydroxy-2[(octadecyloxy)methyl]-4H—pyran-4-one<br>Analysis calc'd for: C$_{24}$H$_{42}$O$_4$: C, 73.05; H, 10.73<br>Found: C, 73.18; H, 10.96 | 82-84 | (CHCl$_3$) 3405, 2918, 2855, 1648, 1630, 1453, 1255, 1050 cm$^{-1}$ | 0.88 (t, 3H), 1.25 (S, 30H), 1.40-1.75 (m, 2H), 3.51 (t, 2H), 4.25 (S, 2H), 6.51 (S, 1H), 7.80 (S, 1H) |
| 15. | (CH$_3$)$_3$C—CO—O-[pyran-4-one]-CH$_2$O(CH$_2$)$_{13}$CH$_3$ | 52-54 | (CHCl$_3$) 2930, 2860, 1762, 1668, 1640, 1195, 1140, 1095 cm$^{-1}$ | 0.88 (t, 3H), 1.26 (S, 22H), 1.36 (S, 9H), 1.45-1.80 (m, 2H), 3.50 (t, 2H), 4.29 (S, 2H), 4.50 (S, 1H), 7.78 (S, 1H) |

TABLE 1-continued

| EXAMPLE NO. | | mp. (°C.) | IR | NMR (CDCl₃) |
|---|---|---|---|---|
| | 4-oxo-2-[(tetradecyloxy)methyl]-4H—pyran-5-yl-2,2-dimethylpropanoate<br>Analysis calc'd for: $C_{25}H_{42}O_5$; C, 71.05, H, 10.02<br>Found: C, 70.84; H, 10.08 | | | |
| 16. | 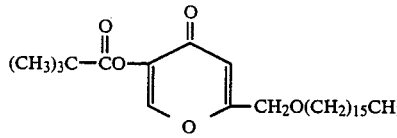<br>2-[(hexadecyloxy)methyl]-4-oxo-4H—pyran-5yl-2,2-dimethylpropanoate<br>Analysis calc'd for: $C_{27}H_{46}O_5$: C, 71.96; H, 10.29<br>Found: C, 71.64; H, 10.27 | 60–61 | (KBr pellet)<br>2918, 2845, 1748,<br>1660, 1640, 1189,<br>1140, 910 cm⁻¹ | 0.88 (t.3H), 1.27 (S, 26H), 1.37<br>(S, 9H), 1.65 (m, 2H), 3.51 (t, 2H)<br>4.28 (S, 2H), 6.46 (S, 1H), 7.78 (S, 1H) |
| 17. | 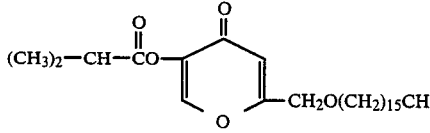<br>2-[(hexadecyloxy)methyl]-4-oxo-4H—pyran-5-yl-2-methylpropanoate<br>Analysis calc'd for: $C_{26}H_{44}O_5$: C, 71.52; H, 10.16<br>Found: C, 71.40; H, 10.08 | 54–55 | (CHCl₃)<br>2930, 2855, 1765,<br>1667, 1638, 1460<br>1140, 1085 cm⁻¹ | 0.88 (t, 3H); 1.27 (S, 26H), 1.33 (d,<br>6H), 1.40–1.75 (m, 2H), 2.84 (septet, 1H)<br>3.50 (t, 2H), 2.27 (S, 2H), 6.46 (S, 1H),<br>7.80 (S, 1H) |
| 18. | 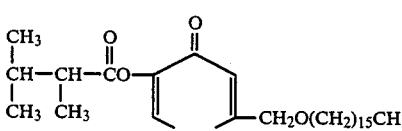<br>2-[(hexadecyloxy)methyl]-4-oxo-4H—pyran-5-yl-2,3-dimethylbutanoate<br>Analysis calc'd for: $C_{28}H_{48}O_5$: C, 72.37; H, 10.41<br>Found: C, 72.46; H, 10.67 | 37.5–39.0 | (CHCl₃)<br>2920, 2845, 1758,<br>1660, 1634, 1460,<br>1188, 1133 cm⁻¹ | 0.87 (t, 3H), 0.99 (d, 3H), 1.06 (d,<br>3H), 1.24 (d, 3H), 1.27 (S, 26H),<br>1.40–1.75 (m, 2H), 2.07 (m, 1H), 2.51<br>(m, 1H), 3.50 (t, 2H), 4.26 (S, 2H),<br>6.46 (S, 1H), 7.79 (S, 1H) |
| 19. | 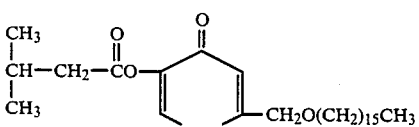<br>2-[(hexadecyloxy)methyl]-4-oxo-4H—pyran-5-yl-3-methylbutansate<br>Analysis calc'd for: $C_{27}H_{46}O_5$: C, 71.96; H, 10.29<br>Found: C, 71.85; H, 10.35 | 55–55.5 | (CHCl₃)<br>2920, 2850, 1765,<br>1663, 1638, 1465<br>1190, 1140 cm⁻¹ | 0.88 (t, 3H), 1.05 (d, 6H), 1.26 (S,<br>26H), 1.40–1.75 (m, 2H), 1.90–2.40<br>(m, 1H), 2.46 (d, distorted, 2H),<br>3.50 (t, 2H), 4.28 (S, 1H), 6.48<br>(S, 1H), 7.82 (S, 1H) |
| 20. | 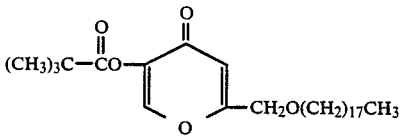<br>2-[(octadecyloxy)methyl]-4-oxo-4H—pyran-5-yl-2,2-dimethylpropanoate<br>Analysis calc'd for: $C_{29}H_{50}O_5$: C, 72.63, H, 10.53<br>Found: C, 72.63, H, 10.77 | 66–67 | (CHCl₃)<br>2930, 2855, 1760,<br>1665, 1640, 1094,<br>1040, 995 cm⁻¹ | 0.88 (t, 3H), 1.25 (S, 30H), 1.34 (S,<br>9H), 1.45–1.75 (m, 2H), 3.50 (t, 2H),<br>4.28 (S, 2H), 6.45 (S, 1H), 7.77 (S, 1H) |
| 21. | 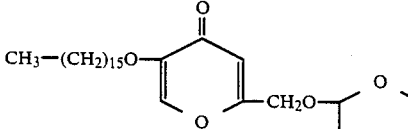<br>5-Hexadecyloxy-2-tetrahydropyranyloxymethyl-4H—pyran-4-one<br>Analysis calc'd for: $C_{27}H_{46}O_5$: C, 71.96; H, 10.29<br>Found: C, 71.56, H, 10.34 | 56–57 | (CHCl₃)<br>3000, 2930, 2860,<br>1655, 1625, 1600,<br>1216, 1200,<br>1038 cm⁻¹ | 0.88 (t, 3H), 1.25 (S, 24H), 1.4–2.0<br>(m, 8H), 3.58 (t, broad, 2H), 3.84<br>(t, 2H), 3.40 (d, 2H), 4.7 (d, broad,<br>1H), 6.46 (S, 1H), 7.52 (S, 1H) |

TABLE 1-continued

| EXAMPLE NO. | | mp. (°C.) | IR | NMR (CDCl$_3$) |
|---|---|---|---|---|
| 22. | 5-Hexadecyloxy-2-hydroxymethyl-4H—pyran-4-one<br>CH$_3$—(CH$_2$)$_{15}$O— [pyranone ring] —CH$_2$OH<br>Analysis calc'd for: C$_{22}$H$_{38}$O$_4$: C, 72.09; H, 10.45<br>Found: C, 71.61; H, 10.57 | 68.9–72 | (CHCl$_3$)<br>3610, 3375, 1655,<br>1622, 1600, 1262,<br>1195 cm$^{-1}$ | 0.88 (t, 3H), 1.26 (S, 26H), 1.5–2.0 (m, 2H), 3.82 (t, 2H), 3.95 (t, 1H) 4.45 (d, 2H), 6.48 (S, 1H), 7.55 (S, 1H) |
| 23. | 5-Hexadecyloxy-4-oxo-4H—pyran-2-hydroxymethyl-2,2-dimethylpropanoate<br>CH$_3$(CH$_2$)$_{15}$O— [pyranone ring] —CH$_2$OC(O)—C(CH$_3$)$_3$<br>Analysis calc'd for: C$_{27}$H$_{46}$O$_5$: C, 71.96; H, 10.29<br>Found: C, 71.87; H, 10.54 | | (CHCl$_3$)<br>2922, 2850, 1738,<br>1650, 1628, 1155,<br>1135 cm$^{-1}$ | 0.88 (t, 3H), 1.26 (S, 30H), 1.4–2.0 (m, 4H), 3.84 (t, 2H), 4.82 (S, 2H), 6.37 (S, 1H), 7.53 (S, 1H) |
| 24. | 5-Hexadecyloxy-2-carboxyl-4H—pyran-4-one<br>CH$_3$(CH$_2$)$_{15}$O— [pyranone ring] —C(O)—OH<br>Analysis calc'd for: C$_{22}$H$_{36}$O$_5$: C, 69.44; H, 9.54<br>Found: C, 69.48; H, 9.72 | 126.5–130.5 | (CHCl$_3$)<br>3550–2250 (broad, OH), 2920, 2848,<br>1730, 1647, 1625,<br>1600, 1238 cm$^{-1}$ | 0.88 (t, 3H), 1.25 (S, 20H), 1.4–2.0 (m, 4H), 3.90 (t, 3H), 5.65–6.25 (broad, 1H), 7.32 (S, 1H), 7.65 (S, 1H) |

Certain of the preferred compounds of the invention were evaluated for biological activity, i.e. elastase inhibitory/anti-inflammatory activity, by determining the elastase inhibitory effects of the compounds pursuant to the following test procedure.

EXAMPLE 22

Inhibition of Human Leukocyte Elastase (HLE)

This test measures the rate of hydrolysis of Methoxy-succinyl-Alanyl-Alanyl-Prolyl-Valyl-nitroanilide by HLE in the presence and absence of the compound to be tested. The procedure used is as follows. The following stock solutions are prepared.

1. a saline solution of HLE prepared from a composition containing 10% HLE with the remainder being sodium acetate (300 micrograms per ml) wherein the concentration was adjusted to give a change in absorption of 0.12 od units per minute in the assay in the absence derivative, 2. a dimethylsulfoxide solution of the nitroanilide peptide (2 m mole), 3. tris-HCl buffer (0.2M, pH 8.0) and 4. a dimethylsulfoxide solution of the derivative to be tested at 20 times the desired final concentration.

The test hydrolysis solution was then prepared by adding 850 microliters buffer, 50 microliters derivative solution, 50 microliters peptide solution to a 1 cm. semi-micro cuvette. The cuvette was capped, slightly shaken and placed in the light chamber of a recording colorimeter where the increase in absorption at 410 nm. due to liberated nitroaniline was measured. Using this procedure, the one minute change in absorption of the test sample containing derivative was compared to the change in absorption in the absence of derivative. A 20% or more decrease in the rate of absorption was interpreted as a positive inhibition.

The results with respect to certain of the preferred compounds of the invention are given in Table II below. The results indicate that the compounds of formulas I, II, and/or III are active at the concentrations indicated.

TABLE II

| Compound Example No. | Inhibition of Elastase (Inhibitory Concentration (Molar) | % Inhibition |
|---|---|---|
| 11 | $2.0 \times 10^{-5}$ | 24 |
| 12 | $1.0 \times 10^{-5}$ | 34 |
|    | $2.0 \times 10^{-5}$ | 48 |
| 13 | $2.0 \times 10^{-5}$ | 23 |
| 14 | $1.0 \times 10^{-5}$ | 46 |
|    | $2.0 \times 10^{-5}$ | 50 |
| 15 | $5.0 \times 10^{-8}$ | 38 |
|    | $2.0 \times 10^{-7}$ | 60 |
|    | $1.0 \times 10^{-5}$ | 81 |
|    | $2.0 \times 10^{-5}$ | 88 |
| 16 | $5.0 \times 10^{-8}$ | 27 |
|    | $2.0 \times 10^{-7}$ | 52 |
|    | $1.0 \times 10^{-6}$ | 69 |
|    | $1.0 \times 10^{-5}$ | 87 |
|    | $2.0 \times 10^{-5}$ | 89 |
| 17 | $5.0 \times 10^{-8}$ | 61 |
|    | $2.0 \times 10^{-7}$ | 81 |
|    | $1.0 \times 10^{-6}$ | 88 |
| 18 | $1.0 \times 10^{-5}$ | 48 |
|    | $2.0 \times 10^{-5}$ | 59 |
| 19 | $1.0 \times 10^{-5}$ | 52 |
|    | $2.0 \times 10^{-5}$ | 67 |
| 20 | $5.0 \times 10^{-6}$ | 69 |
|    | $1.0 \times 10^{-5}$ | 73 |
|    | $2.0 \times 10^{-5}$ | 66 |
| 21 | $2.0 \times 10^{-5}$ | 23 |
| 23 | $5.0 \times 10^{-6}$ | 36 |
|    | $1.0 \times 10^{-5}$ | 62 |
|    | $2.0 \times 10^{-5}$ | 65 |
| 24 | $5.0 \times 10^{-6}$ | 84 |

TABLE II-continued

| Compound Example No. | Inhibition of Elastase (Inhibitory Concentration (Molar)) | % Inhibition |
|---|---|---|
| | $1.0 \times 10^{-5}$ | 83 |
| | $2.0 \times 10^{-5}$ | 86 |

While the invention has been described and illustrated with reference to certain preferred embodiments thereof, those skilled in the art to which the invention pertains will appreciate that various changes, modifications and substitutions can be made therein without departing from the spirit of the invention. For example, effective dosages other than the preferred ranges set forth hereinabove may be applicable as a consequence of variations in the responsiveness of the patient being treated, severity of the inflammatory condition, i.e., emphysema, rheumatoid arthritis and similar elastase mediated conditions, dosage dependent adverse effects, if any, observed and analogous considerations. Likewise, the specific pharmacological response observed may vary depending upon the particular active compounds selected or whether different active compounds are used in combination or in the presence of suitable pharmaceutical carriers, as well as the type of formulation and mode of administration employed, and such expected variations or differences in results are specifically contemplated in accordance with the objects and practices of the present invention. It is intended, therefore, that the invention be limited only by the scope of the claims which follow.

What is claimed is:
1. A compound of the formula

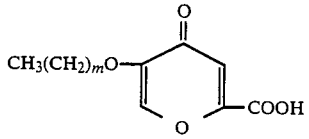

wherein m is 13 to 17, inclusive.

2. A compound according to claim 1 of the formula

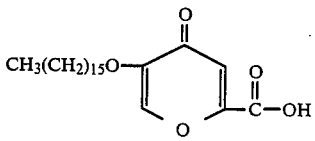

3. A pharmaceutical composition for promoting an elastase inhibitory anti-inflammatory effect in a mammal in need thereof comprising an elastase inhibitory anti-inflammatory effective amount of at least one compound according to claim 1 in combination with a pharmaceutical carrier therefor.

4. A method of promoting an elastase inhibitory anti-inflammatory effect in a mammal in need thereof comprising administering thereto an elastase inhibitory anti-inflammatory effective amount of at least one compound according to claim 1 or a pharmaceutically acceptable salt thereof.

* * * * *

UNITED STATES PATENT AND TRADEMARK OFFICE
CERTIFICATE OF CORRECTION

PATENT NO. : 4,812,474

DATED : March 14, 1989

INVENTOR(S) : Campbell, et al.

It is certified that error appears in the above-identified patent and that said Letters Patent is hereby corrected as shown below:

Column 4, line 8, reading "enzyme" should read -- enzymes --.
Column 4, line 37, reading "liber" should read -- liver --.
Column 17, Table 1-continued, Example 20, the first line below the structure, reading "2,[(octadecyloxy)" should read -- 2-[(octadecyloxy) --.
Column 17, Table 1-continued, Example 20, the third line below the structure, reading "72.63" should read -- 72.76 --.

Signed and Sealed this

Fifth Day of March, 1991

Attest:

HARRY F. MANBECK, JR.

Attesting Officer

Commissioner of Patents and Trademarks